United States Patent [19]

Beacco et al.

[11] 4,230,854
[45] Oct. 28, 1980

[54] ANALOGUES OF ERGOT ALKALOIDS

[75] Inventors: Enzo Beacco, Limbiate; Maria L. Bianchi, Milan; Annacleto Minghetti, Milan; Celestino Spalla, Milan, all of Italy

[73] Assignee: Societa Farmaceutici Italia S.p.A., Milan, Italy

[21] Appl. No.: 888,750

[22] Filed: Mar. 21, 1978

[30] Foreign Application Priority Data

Apr. 19, 1977 [GB] United Kingdom .............. 16096/77

[51] Int. Cl.$^2$ ........................................... C07D 511/02
[52] U.S. Cl. ............................... 544/346; 204/158 R; 424/250; 435/118
[58] Field of Search .................... 544/346; 424/261

[56] References Cited

U.S. PATENT DOCUMENTS

| 3,666,762 | 5/1972 | Guttmann et al. | 544/346 |
| 3,772,299 | 11/1973 | Stadler et al. | 544/346 |
| 4,000,139 | 12/1976 | Stutz et al. | 544/346 |
| 4,101,552 | 7/1978 | Mago et al. | 424/261 |
| 4,124,712 | 11/1978 | Stutz et al. | 544/346 |

FOREIGN PATENT DOCUMENTS 2700234 7/1977 Fed. Rep. of Germany .......... 544/346

*Primary Examiner*—Mary C. Lee
*Attorney, Agent, or Firm*—Oblon, Fisher, Spivak, McClelland & Maier

[57] ABSTRACT

Ergot alkaloids having interesting pharmacological activities, for instance in the therapy of migraine or hypertension. Such compounds are obtained in a fermentative process using mutant strains of Claviceps purpurea eventually hydrogenating the products thus obtained.

1 Claim, No Drawings

ANALOGUES OF ERGOT ALKALOIDS

The present invention relates to new ergot alkaloids, which are not found in nature and to a fermentative process with particular mutant strains of *Claviceps purpurea* in the presence of suitable aminoacids as precursors.

These precursors, which are added to the broth during fermentation, may be either naturally occurring amino acids or artificially prepared derivatives thereof.

More particularly, the present invention concerns new ergot alkaloids of the structure:

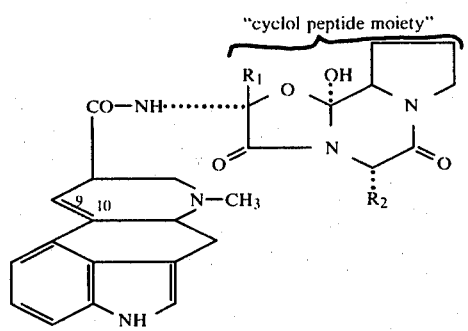

and their 9,10 dihydroderivatives, wherein $R_1$ is selected from the group consisting of methyl, ethyl and isopropyl;

$R_2$ is a radical selected from the group consisting of

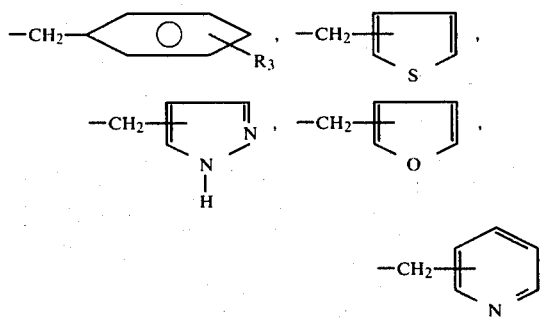

unsubstituted linear $C_3$–$C_5$ alkyl-group, halogen-substituted linear $C_3$–$C_5$ alkyl-group and halogen-substituted isobutyl-group, $R_3$ being a radical selected from the group consisting of $C_1$–$C_4$ alkyl, $C_1$–$C_4$ alkoxy and halogen.

A further object of the invention is the fermentative process for the preparation of the new ergot alkaloids of the structure (I), which comprises mutagenous processes for obtaining peculiar mutant strains of *Claviceps purpurea* which are thus suitably made dependant from particular aminoacids, and the use of said mutant strains of *Claviceps purpurea* in the presence of selected aminoacids which are added to the fermenting broth, so to produce the desired new ergot alkaloids of the structure I, which are isolated and purified according to methods known "per se".

The new ergot alkaloids of the structure (I) show interesting pharmacological activities, shown in the following Table I, which depend on the $R_1$ and $R_2$ radicals and moreover the activities may vary whether the double bond in 9–10 position is present or removed by hydrogenation.

For instance the new derivatives (I) wherein $R_1$ is a $CH_3$ and $R_2$ is a substituted benzyl exhibit vaso-constricting activity and therefore they may be employed in the therapy of migraine. On the other hand the new derivatives (I) wherein $R_1$ is an isopropyl and $R_2$ is either a substituted benzyl or an aliphatic chain and where also the double bond in 9–10 is hydrogenated exhibit adrenolytic activity and activities on the Central Nervous System and therefore they may be used in the therapy of hypertension.

| Compound | α-adrenergic blockade | | $LD_{50}$ (mouse) (c) mg/Kg i.v. |
| --- | --- | --- | --- |
| | In vitro (a) $IC_{50}$ mcg/ml | In vivo (b) $ED_{50}$ mg/Kg i.v. | |
| Ergotamine | 0.07 | 0.2 | 70 |
| 5'-debenzyl-5'-p-chlorobenzyl ergotamine | 0.03 | 0.1 | 100 |
| Dihydroergotamine | 0.02 | 0.08 | 118 |
| 5'-debenzyl-5'-p-chlorobenzyl dihydroergotamine | 0.02 | 0.05 | 150 |
| Dihydroergocristine | 0.05 | 0.03 | 174 |
| 5'-debenzyl-5'-p-chlorobenzyl dihydroergocristine | 0.03 | 0.02 | 190 |

(a) α-receptors blockade was determined against the spasmogenic effect of epinephrine on the isolated guinea-pig seminal vescicle according to Brugger J. (Helv.-Physiol. Acta 3, 117, 1945). Concentration producing 50% inhibition of the effect of the agonist were estimated graphically for each antagonist.

(b) α-receptor blockade was determined in rats according to Luduena F.P. et al. (Arch. Int. Pharmacodyn CXXII, 111, 1959). $ED_{50}$ is the graphically estimated dose of antagonist protecting 50% of animals from the lethal effect of 0.2 mg/Kg epinephrine, injected i.v. 5 min later.

(c) $LD_{50}$ was determined in mice according to the standard procedure. (From Table 1 it appears that the three new derivatives display, in comparison with the parent compounds, an increased α-adrenolytic activity both "in vitro" and "in vivo". On the other hand the acute toxicity is somewhat reduced).

It is well known that ergot alkaloids (I) are amides of lysergic acid, containing a cyclol peptide moiety biosynthetically derived from a suitable condensation of 3 amino acids, one of which, i.e. proline, is present in all of them. The cyclol residue consists, respectively, in the case of ergotamine ($R_1$=$CH_3$; $R_2$=$CH_2C_6H_5$) of one molecule of phenylalanine and of one of alpha-hydroxyalanine; in the case of ergocristine ($R_1$=$CH(CH_3)_2$; $R_2$=$CH_2C_6H_5$) of one molecule of phenyl-alanine and one of an alphahydroxyvaline; in the case of ergocryptine ($R_1$=$CH(CH_3)_2$; $R_2$=$CH_2CH(CH_3)_2$) of a molecule of leucine and one of alpha-hydroxyvaline.

It was surprisingly found that strains of *C. purpurea*, previously treated with a mutagenic agent and made unable to grow in the absence of non-hydroxylated aminoacids (i.e. phenyl-alanine or leucine), are able to produce alkaloids that contain as terminal amino acid the analogue present in the medium, when grown in the presence of the amino acid for which they have been mutagenously made dependent and of analogues thereof. It is possible to obtain remarkably high yields of the alkaloid containing the amino acid analogue, by adding small amounts of the amino acid required by the strain in the first stage of the fermentation, which is known as "trophophase", and by subsequent addition of large amounts of the analogue in the second stage of the fermentation, which is known as "idiophase".

The strains employed are the well-known producers of ergot alkaloids in submerged culture, which have been described by several authors (Spalla C. in Genetic of Ind. Microorganisms, Academia Prague 1973, 393, 1973; Floss H. G. et al., Phytochemistry, vol. 8, 141, 1974). Specifically the strains that can be used are: *C. Purpurea* ATCC 15383, producer of ergotamine and described in U.S. Pat. No. 3,276,972; *C. purpurea* ATCC 20103, producer of ergocristine and described in U.S. Pat. No. 3,567,583, and *C. purpurea* ATCC 20019, producer of ergocryptine and described in U.S. Pat. No. 3,485,722.

The mycelial mat of a slant from strains producers of either ergotamine or ergocristine or ergocryptine is suspended into sterile water and broken in very short fragments by shaking in a Waring blendor and filtered through silk organzine. The filtrate, which contains almost unicellular fragments, is irradiated with U.V. light in order to obtain a mortality of 90–99%. The suspension is diluted in sterile water and plated out in Petri dishes onto a solid medium, additioned with the amino acid for which requiring mutants are searched (i.e. leucine or phenylalanine). After a proper incubation time, the grown colonies are transferred by the well-known technique into a medium not containing the amino acid for which requiring mutants are searched. The strains able to grow in the former medium and unable to grow in the latter are dependent on the amino acid. They are maintained by successive transfers onto a medium containing the amino acid.

For the production of the alkaloid analogues the requiring mutants are grown in a liquid medium containing a source of carbon, one of nitrogen, one of phosphor, one of sulphur and of several mineral salts as well as the amino acid which the strain requires. The amount of the amino acid varies between 0.5 and 2 g/l according to the case. After an incubation time ranging from 3 to 5 days the culture is additioned with an analogue of the amino acid required by the strain at a level ranging from 3 to 6 g/l and furtherly incubated for 9–11 days more to reach a limit of 14 days. The cultivation, also called fermentation, can be made either in shaken flasks or in fermentors of various sizes.

At the end of the fermentation the broth cultures contain the analogue of the alkaloid and small amounts of the normal alkaloid as well. The alkaloid analogue is extracted as follows.

The broth is filtered and the mycelium is extracted several times with a 4% aqueous solution of tartaric acid. After filtration, the aqueous phase is made alkaline to pH 9 with sodium hydroxide and extracted with methylene chloride.

The organic phase is concentrated, precipitated and crystallized as salt of phosphoric acid. From the phosphate the free base is obtained and furtherly enriched with the analogues of natural alkaloids by chromatography on silicagel column.

The separation of the new products from the natural ones is then achieved by fractionated crystallization.

The alkaloid concentration is determined spectrophotometrically after colouring by Van Urk reagent and reading at =550 mu.

The ratios between the natural and substituted amino acids present in the peptide moiety are reckoned by means of the acid hydrolysis of the alkaloid and by the quantitative determinations of the single amino acids.

In order to identify the final products the usual methods of instrumental analysis (NMR, IR, MS, UV, etc.) are employed.

The phenylalanine-requiring mutants of strains producers of ergocristine or of ergotamine can produce alkaloid analogues, which incorporate into the site of phenylalanine a phenylalanine molecule substituted in the benzene ring with halogens, alkyls, alkoxyls. They can also produce alkaloids incorporating into the site of phenylalanine its isosters like thienylalanine, alfa- and beta-pyrazolyl-alanine, furylalanine, pyridylalanine.

The leucine-requiring mutants of strains producers of ergocryptine can produce alkaloid analogues which incorporate into the site of leucine a molecule of linear alfa-amino acids with 2 to 7 C atoms. They can also produce alkaloids incorporating into the site of leucine natural amino acids substituted with halogen atoms like 5,5,5 trifluoroleucine.

EXAMPLE 1

5'-debenzyl-5'-p-chlorobenzylergocristine

The mycelial mat of a 12-day slant on solid medium "pep 3" (see the accompanying Table II) of strain ATCC 20103 of *C. purpurea*, producer of ergocristine in submerged culture, was transferred into 50 ml of distilled sterile water and fragmentized in a waring blendor for 20 sec. The suspension was filtered through silk organzine and 5 ml of the filtrate was exposed to the light ($520\mu$ watt/cm$^2$) of a U.V. lamp for 45 sec. The treated suspension, after proper dilution, was plated out onto solid medium TM (see Table II) additioned with 1% phenylalanine, in Petri dishes. The plates were incubated at 28° C. for 10–12 days. The grown colonies were transferred by the replica-plating well-known method (Lederberg, J. Bacy. 63, 399, 1952) onto solid medium TM in Petri dishes and the plates were incubated at 28° C. for 10–12 days.

Out of the screening of 3,000 colonies 4 strains were found unable to grow on minimal medium TM. These strains were confirmed by isolation in medium TM as well as in medium TM additioned with phenyl-alanine and 2 of them proved to be strictly phenyl-alanine dependent mutants.

Ten 300 ml flasks, each containing 50 ml of medium TG (see the Table II) additioned with 1 g/l of phenylalanine and sterilized 100° C. per 30 min. were inoculated singly with a portion of mycelial mat corresponding to approximately a square cm from a slant of solid medium "pep 3" of the mutant strain. These flasks were incubated at 23° C. for 4 days on a rotating shaker, at 225 r.p.m. describing a circle with 5 cm diameter. These flasks corresponded to the vegetative phase. Fifty 300-ml flasks, each containing 40 ml of medium T25 (see the Table II), additioned with 1 g/l of 1-phenylalanine and sterilized at 105° C. per 25 min. were inoculated each with 5 ml of the vegetative-culture and were incubated at 23° C. on the same shakers used for the vegetative phase. After 4 days the flasks were additioned with 4 g/l of p-chlorophenylalanine.

After further 10 days' incubation the cultures were pooled, thus obtaining about 2 liters of broth, which yielded 700 mcg/ml of total peptide alkaloids. These were extracted as follows.

Extraction of
5'-debenzyl-5'-p-chlorobenzyl-ergocristine

The broth culture was filtered, the filtrate was discarded and the mycelium was suspended into a 5% aqueous solution of tartaric acid. After vigorous shaking and filtration, the precipitate was reextracted twice. The collected together filtrates were made alkaline to pH 9 with 20% NaOH and extracted with methylene chloride several times. The organic phase was washed with water, concentrated and precipitated with hexane. The crude base thus obtained (0.9 g) was decolorized with active carbon, dissolved into 10 ml of 95% ethanol and additioned with a 0.8 ml of 75% $H_3PO_4$. The solution was refluxed in the dark for 30 min. and finally left standing at 3° C. for 5 days.

In this way a phosphate (0.5 g) crystallized, which contained a mixture of ergocristine (20%) and of 5'-debenzyl-5'-p-chlorobenzylergocristine (80%). From the phosphate the crude base was obtained by alkalization and extraction with $CH_2Cl_2$ and was crystallized again from acetone. The crystallized product was chromatographed on a silica-gel column eluting with a mixture of $CHCl_3$ and methanol (starting ratio: 99:1, final one: 90:10). After discarding the fractions containing the dextrorotatory isomers, the fraction enriched with 5'-debenzyl-5'-p-chlorobenzylergocristine was recovered. By successive crystallizations from benzene, methanol, acetone, the sought product (100 mg) was isolated. In the MS analysis it showed its characteristic fragments and m/e: 376 and 378; 278 and 280; 267, 153, 70. The acid hydrolysis of the peptide moiety yielded the amino acids proline and p-chlorophenylalanine in ratio 1:1. Its alkaline hydrolysis yielded lysergic acid and 3,3 dimethylpyruvic acid.

EXAMPLE 2

A mutant strain obtained by UV-light treatment as in Example 1 was used to inoculate 8 flasks of medium TG in the same conditions of Example 1. At the end of the vegetative phase these flasks were pooled, thus obtaining 400 ml of brothculture, and were used to inoculate a 10-liter fermentor, containing 6 liters of medium T25 additioned with 1% phenylalanine. The fermentor was provided with an impeller of the discoturbine type, with an aeration corresponding to 0.5 liters/liter/min. and with a stroke of 600 r.p.m. The incubation temperature was 23° C. Four days after the beginning of the fermentation the culture was additioned with 4% p-chlorophenylalanine. The broth culture was harvested on the 13th day of fermentation.

The contents in total peptide alkaloids corresponded to 600 mcg/ml, 65% of which resulted to be 5'-debenzyl-5'-p-chlorobenzylergocristine. The extraction procedure was the same of Example 1.

EXAMPLE 3

The same strain of example 1 was fermented in flasks in the same conditions of Example 1 both in the vegetative and in the productive phases, with the only difference in the addition of p-fluorophenylalanine on the 4th day of fermentation. On the 14th day of fermentation the extracted broth yielded 750 mcg/ml of total peptide alkaloids, 80% of which resulted to be 5'-debenzyl-5'-p-fluorobenzylergocristine.

EXAMPLE 4

Strain ATCC 15383, producer of ergotamine, was treated with UV-light in the conditions of Example 1. The treatment resulted in 2 phenylalanine-dependent mutants out of a total of 2.000 scanned colonies.

One of these strains was used as inoculum for a flask fermentation in the same conditions of Example 1 both for the vegetative and the productive phases. On the $4^{th}$ day of the productive phase 4% p-chlorophenylalanine was added. The broths on the $14^{th}$ day yielded 900 mcg/ml of total peptide alkaloids, 80% of which resulted to be 5'-debenzyl-5'-p-fluorobenzylergotamine.

EXAMPLE 5

Strain ATCC 20019, producer of ergocryptine, was treated with UV-light as in Example 1. The treatment yielded 3 leucine-dependent mutants out of 4,000 scanned colonies.

One of these strain was fermented in the conditions and in the media described in Example 1 with the only difference that the aminoacid additioned in the vegetative and the productive phases was respectively 1 g/l and 2 g/l L-leucine. On the $4^{th}$ day of the productive phase 6 g/l of L-norvaline were added. On the $14^{th}$ day the broths contained 1,000 mcg/ml of total peptide alkaloids, 80% of which was 5'-deisobutyl-5'-n-propylergocryptine.

EXAMPLE 6

The leucine-dependent strain used in Example 5, fermented in flasks in the same conditions both in the vegetative and in the productive phases, was additioned with 3 g/l of 5,5,5-trifluoroleucine on the $4^{th}$ day of the productive phase. On the $14^{th}$ day of fermentation the broths were pooled and extracted according to the general method described previously. Their yield was 600 mcg/ml of total peptide alkaloids, with a 60% incorporation of trifluoroleucine.

|  | MEDIA | | | |
|---|---|---|---|---|
|  | pep 3 | TM | TG | T 25 |
| glucose | — | — | 100 | — |
| saccarose | g 300 | 100 | — | 300 |
| L-asparagine . $H_2O$ | — | 10 | — | — |
| anhydrous citric acid | — | — | 10 | 15 |
| $KH_2PO_4$ | 0.5 | 0.5 | 0.5 | 0.5 |
| $MgSO_4 7H_2O$ | 0.5 | 0.3 | 0.3 | 0.5 |
| Yeast extract | — | — | 0.1 | 0.1 |
| KCl | — | — | — | 0.12 |
| $FeSO_4 . 7H_2O$ | 0.007 | 0.007 | 0.007 | 0.007 |
| $ZnSO_4 . 7H_2O$ | 0.006 | 0.006 | 0.006 | 0.006 |
| peptone | 10 | — | — | — |
| agar | 20 | 18 | — | — |
| $NH_4OH$ | — | — | to pH 5.2 | to pH 5.2 |
| NaOH | — | to pH 5.2 | — | — |
| Tap water Distilled | — | — | to 1000 ml | to 1000 ml |

| | MEDIA | | | |
|---|---|---|---|---|
| | pep 3 | TM | TG | T 25 |
| water | to 1000 ml | to 1000 ml | — | — |
| sterilization | 110° C. × 20 min. | 110° C. × 20 min. | 110° C. × 30 min. | 105° C. × 25 min. |

What we claim is:
1. Ergot alkaloids of formula

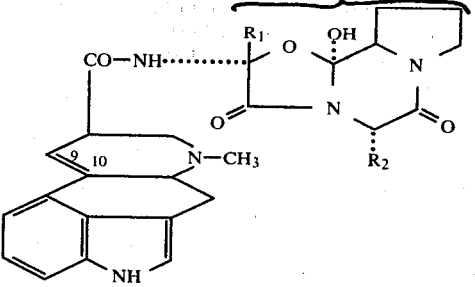

and their 9,10 dihydroderivatives, wherein
$R_1$ is selected from the group consisting of methyl, ethyl and isopropyl;
$R_2$ is selected from the group consisting of

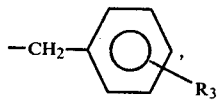

halogen-substituted linear $C_3$–$C_5$ alkyl-group and halogen-substituted isobutyl-group;
$R_3$ being selected from the group consisting of $C_1$–$C_4$ alkyl and halogen.

* * * * *